(12) United States Patent
Harrison (10) Patent No.: US 6,939,367 B2
(45) Date of Patent: Sep. 6, 2005

(54) APPARATUS FOR SELF-APPLIED HOT STONE THERAPY

(76) Inventor: Fred Harrison, 525 Battery Pl., No. 10, Chattanooga, TN (US) 37403

( * ) Notice: Subject to any disclaimer, the term of this patent is extended or adjusted under 35 U.S.C. 154(b) by 15 days.

(21) Appl. No.: 10/602,055

(22) Filed: Jun. 24, 2003

(65) Prior Publication Data
US 2004/0267341 A1 Dec. 30, 2004

(51) Int. Cl.$^7$ .................................................. A61F 7/00
(52) U.S. Cl. ........................................ 607/109; 607/108
(58) Field of Search ............................ 606/204, 204.15; 601/128, 134, 135, 151; 607/96, 104, 108–112, 114, 113

(56) References Cited

U.S. PATENT DOCUMENTS

| 4,033,342 | A | * | 7/1977 | Lake ........................ 128/201.18 |
| 5,007,252 | A | * | 4/1991 | Mochizuki ........................ 63/3 |
| 5,656,019 | A | * | 8/1997 | Cook et al. .................. 601/128 |
| 5,848,981 | A | * | 12/1998 | Herbranson .................. 601/134 |
| 6,412,303 | B1 | * | 7/2002 | Lee ................................. 63/3 |
| 6,629,434 | B2 | * | 10/2003 | Chia et al. ...................... 63/26 |

FOREIGN PATENT DOCUMENTS

| DE | 19639312 | 4/1997 |
| JP | 2000202037 | 7/2000 |

OTHER PUBLICATIONS

"TH.STONE™ Stone Massage Products" http://www.th-stone.com/products_facial.html, 2 pages.

* cited by examiner

Primary Examiner—Linda C. M. Dvorak
Assistant Examiner—Aaron Roane (57) ABSTRACT

The invention is directed to a hot stone therapy apparatus for self-applied hot stone therapy. The apparatus comprises at least one elongated flexible member, and a plurality of stones connected to each other by means of the at least one elongated flexible member. The stones are capable of storing heat energy from, for example, a bowl of hot water. The distribution of the plurality of stones permit self-application of the stones about a desired area of a person's body such as the shoulders, neck, or hips of a person.

1 Claim, 13 Drawing Sheets

APPARATUS FOR SELF-APPLIED HOT STONE THERAPY

BACKGROUND OF THE INVENTION

1. Field of the Invention

The present invention relates to hot stone therapy. More specifically, the invention relates to an apparatus for self-applied hot stone therapy.

2. Description of the Related Art

Thermal treatment is sometimes used to help relax and alleviate muscle stress and thereby reduce muscle pain. Therapeutic devices such as pads that can be heated and applied to a muscle area are known. The use of stones to massage areas of the human body is also known. Such pads and stones are used in a static mode. For example, a person is obliged to remain still after applying a heated therapeutic device, such as a heated pad, to the muscles in the back of their neck. If the person gets up and walks about the heated pad may fall off unless held in place by the person. Thus, there is a need for a hot therapy apparatus that can be used without severely restricting the movements of the user.

Stone kits for treating body surface tissue are known. For example, TH.STONE® supply stone facial products that include various sized individual stones that can be heated or chilled and applied to the body surface (see, e.g., URL: http://www.thstone.com/products_facial.html). A person intent on using such stones must apply a considerable amount of dedicated hand and finger movements. For example, a person desiring to massage the muscles of their neck using a stone would use one or both of their hands to contact the stone with their neck muscles to achieve the desired effect. Thus, there is a need for a therapy apparatus that can be used without requiring substantial use of the person's hands.

Flexible containers with fillings that can store heat are known. For example, German Pat. No. DE19639312 issued to Kirschke describes a cushion having a filling that stores heat. The filling can comprise natural materials such as cherry stones, millet seeds and/or millet husks. The Kirschke device can be attached to the body of a patient using a cushion holder device comprising shoulder straps. While the filling material may not be suitable to make direct contact with a person's skin, direct contact with heated stones with varying textures and degrees of smoothness or roughness can be beneficial and comforting to a person requiring or desiring such contact. Thus, there is a need for an apparatus that directly applies heated stones to a person's body.

Japanese Pat. No. JP2000202037 issued to A. Norio describes a navel pad having permanent magnets and natural stones mounted on a belt that is wound around the belly of the user. The Norio apparatus is not used to treat muscle groups around other parts of the body. Thus, there is a need for an apparatus that directly applies heated stones to various parts of the human body.

None of the above inventions and patents, taken either singly or in combination, is seen to describe the instant invention as claimed. Thus, an apparatus for self-applied hot stone therapy solving the aforementioned problems is desired.

SUMMARY OF THE INVENTION

The invention is directed to a hot stone therapy apparatus for self-applied hot stone therapy. The apparatus comprises at least one elongated flexible member, and a plurality of stones connected to each other by means of at least one elongated flexible member. The stones are capable of storing heat energy from, for example, a bowl of hot water. The distribution of the plurality of stones permit self-application of the stones about a desired area of a person's body such as the shoulders, neck, or hips of a person.

Accordingly, it is a principal object of the invention to provide an apparatus for hot stone therapy.

It is another object of the invention to provide a hot stone therapy apparatus that can be used without severely restricting the movements of the user.

Still another object of the invention is to provide a hot stone therapy apparatus that does not require excessive use of a user's hands.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention relates to hot stone therapy. More specifically, the invention relates to an apparatus for self-applied hot stone therapy.

Referring to the figures in general, the hot stone therapy apparatus is denoted by the reference numeral 100 as a whole. The hot stone therapy apparatus 100 comprises at least one elongated flexible member 120, and a plurality of stones 140 connected in series to each other by means of the at least one elongated flexible member 120.

The stones are denoted generally by the reference numeral 140, individual stones are denoted by the reference numeral 140 followed by a letter, e.g., 140a. The stones 140 are capable of storing heat energy from, for example, hot water. The stones 140 are distributed in such a manner to enable the hot stone therapy device 100 to be mounted on a person's body 180 to provide heat at desired points on the person's body 180.

The stones 140 are preferably natural river stones. Alternatively, the stones 140 may be artificial. The surface 145 of each stone 140 can be varied to provide a range of surface textures to suit different users. For example, the surface 145 of a natural or artificial stone may be artificially roughed or smoothed to achieve a desired degree of smoothness or roughness.

Figure 1:
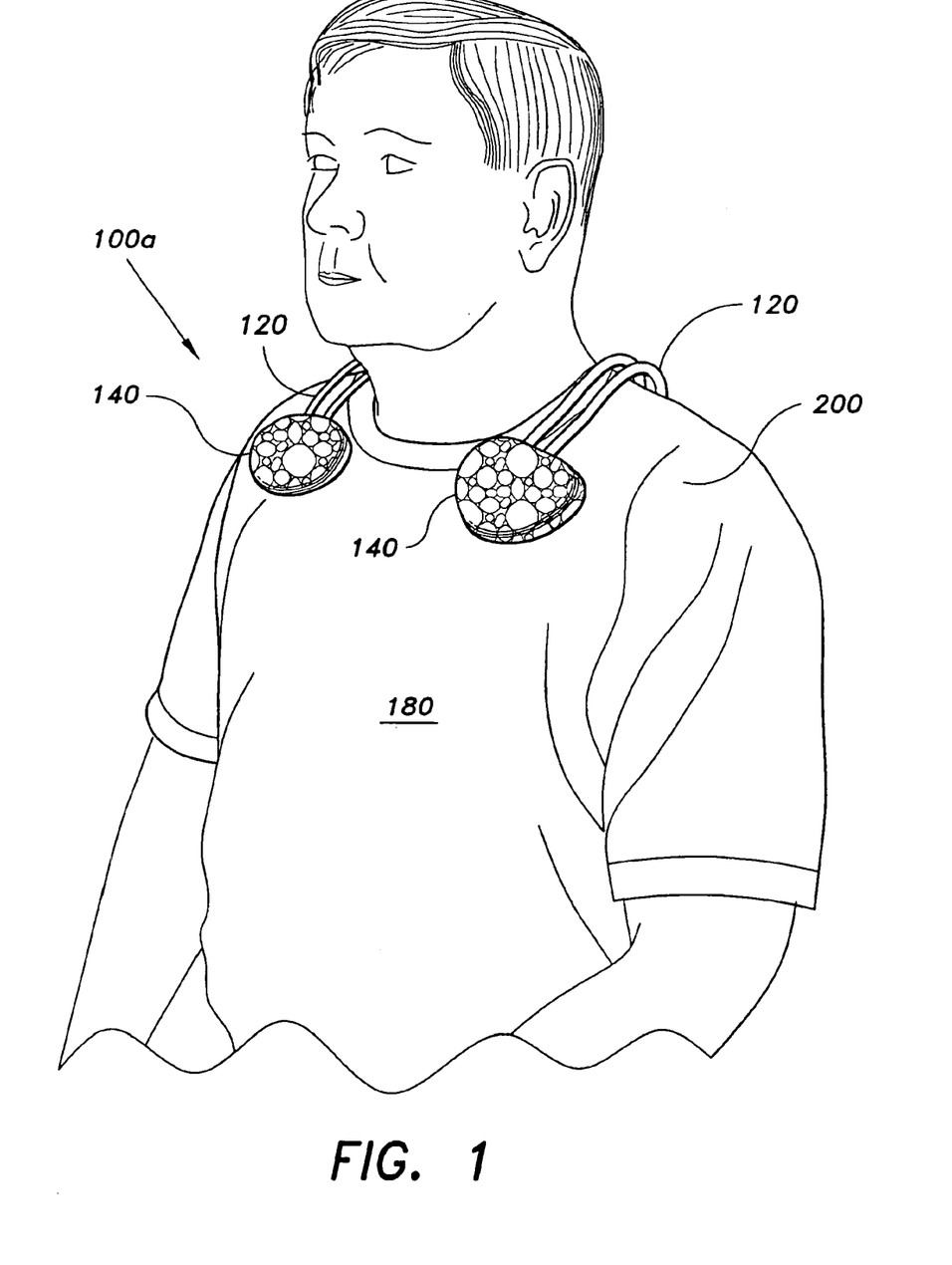
FIG. 1 is a front environmental perspective view of a hot stone therapy apparatus adapted to apply hot stone therapy to a person's shoulders according to a first embodiment of the invention.
Figure 2:
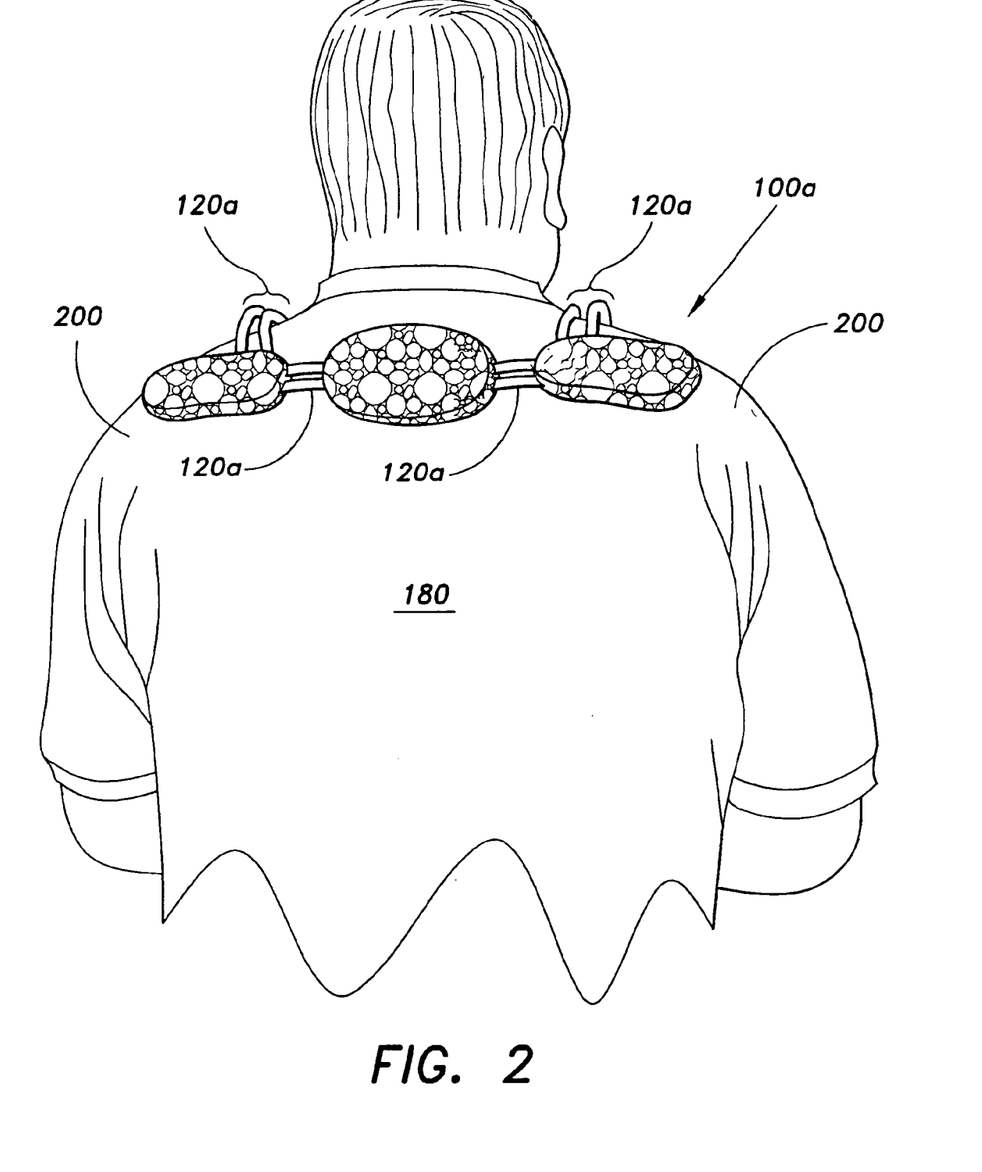
FIG. 2 is a rear view of the hot stone therapy apparatus of FIG. 1.
Figure 3:
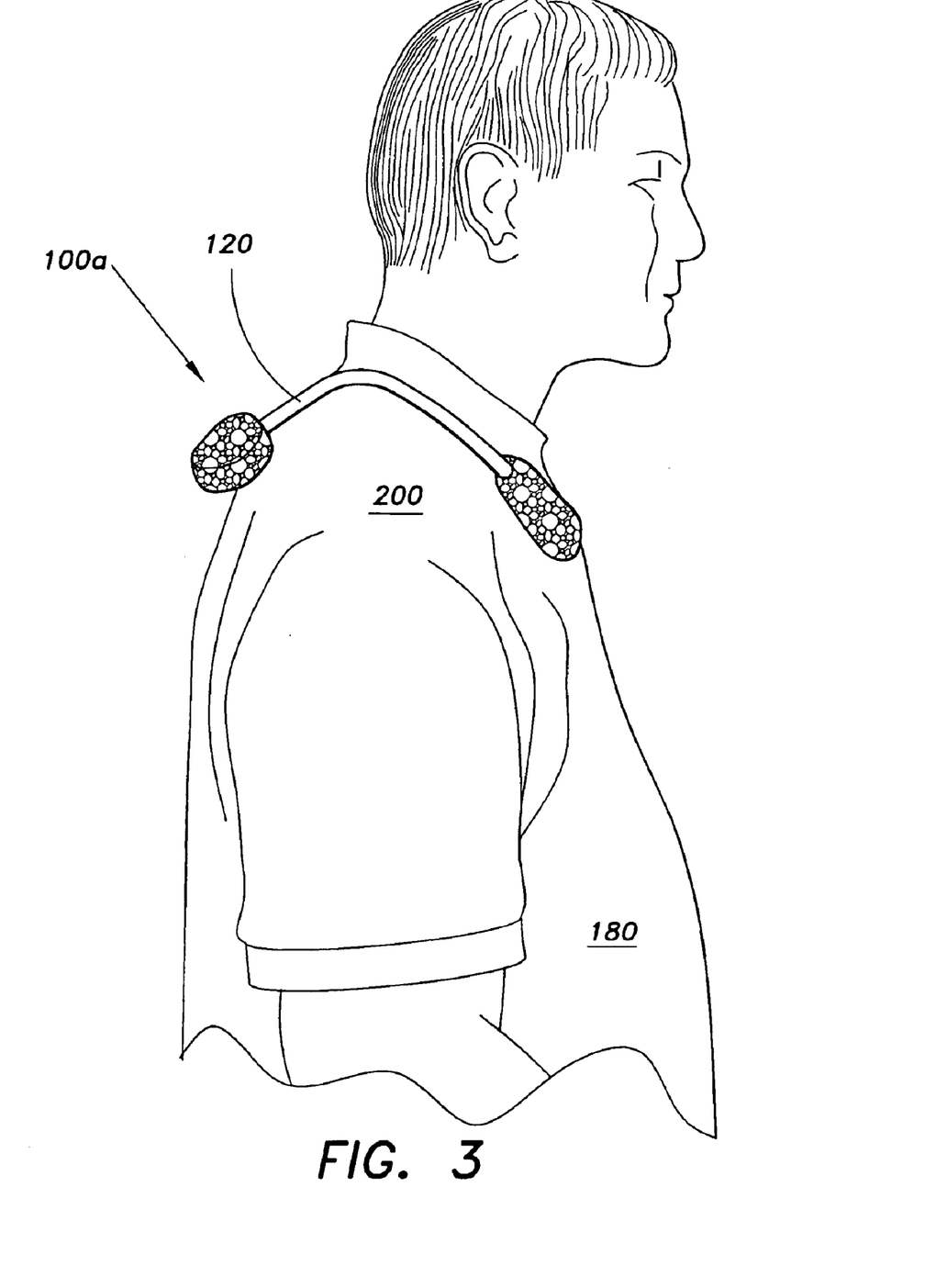
FIG. 3 is a side view of the hot stone therapy apparatus of FIG. 1.

FIGS. 1, 2 and 3 are environmental perspective views of a first embodiment of the invention in which the hot stone therapy apparatus 100 takes the form of a shoulder hot stone therapy apparatus 100a. The shoulder hot stone therapy apparatus 100a is configured to apply hot stone therapy to a person's shoulders 200. In this embodiment of the present invention, the stones 140 are distributed in such a manner as to enable the hot stone therapy device 100a to be mounted on a person's (i.e. wearer's) shoulders 200 without substantially affecting the mobility of the wearer 180. For example, the wearer 180 is free to walk about or sit upright while the hot stone apparatus 100a is on the person's shoulders 200. When the wearer 180 walks about the stones 140 can rub against the shoulders 20p and thereby knead the person's shoulder area 200 without requiring undue use of the wearer's hands. The terms "wearer", "user", and "person" are hereinafter regarded as equivalent terms.

The at least one elongated flexible member 120 is preferably sufficiently stiff to keep the stones 140 in place and sufficiently flexible to enable a person 180 to juxtaposition the stones 140 to suit the wearer's body and thereby make contact at desired points on the wearer's body 180. The at least one elongated flexible member 120 may form a duplex arrangement 120a as shown in FIG. 2.

Figure 4:
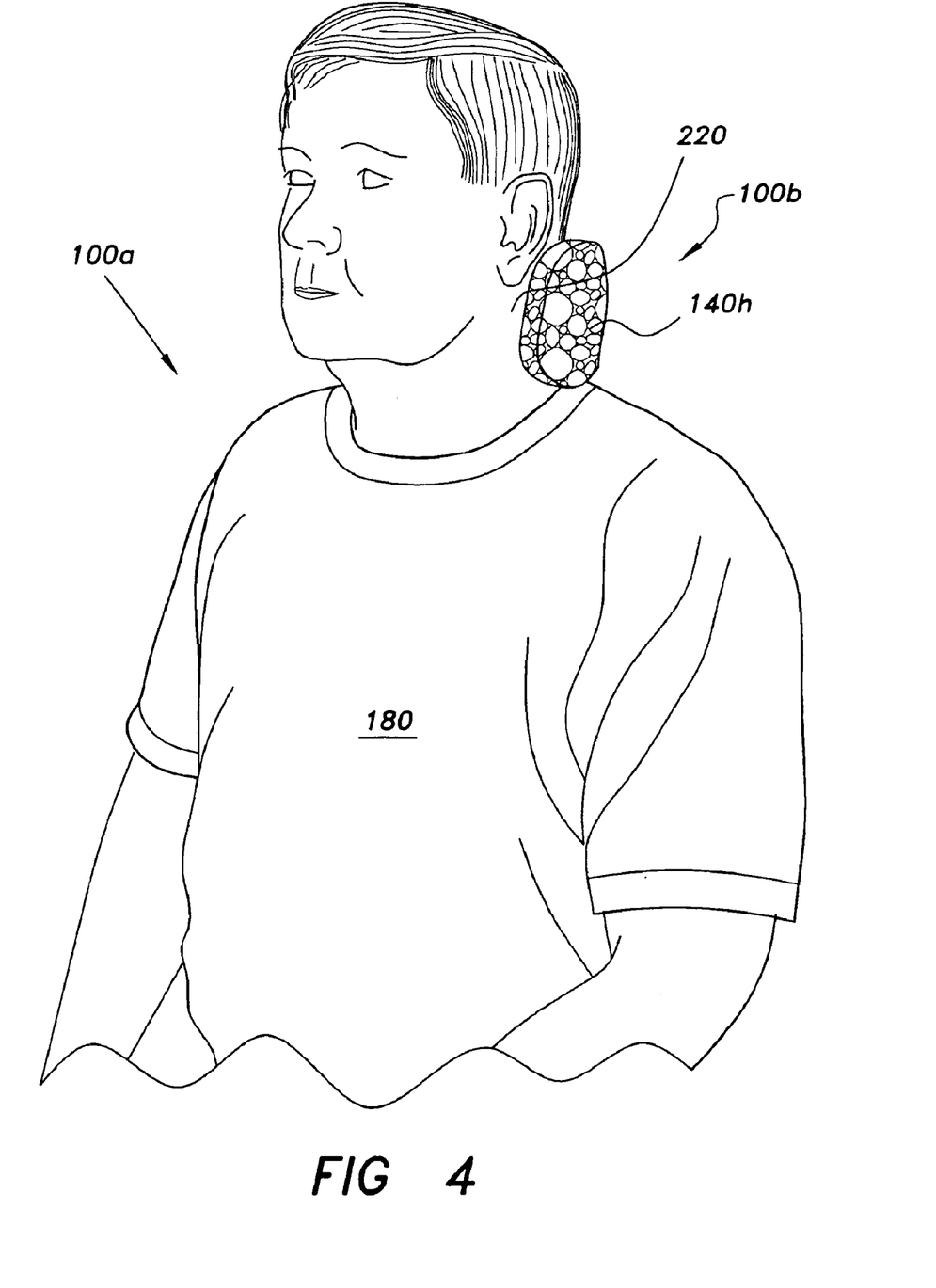
FIG. 4 is a front environmental perspective view of a hot stone therapy apparatus adapted to apply hot stone therapy to a person's neck according to a second embodiment of the invention.
Figure 5:
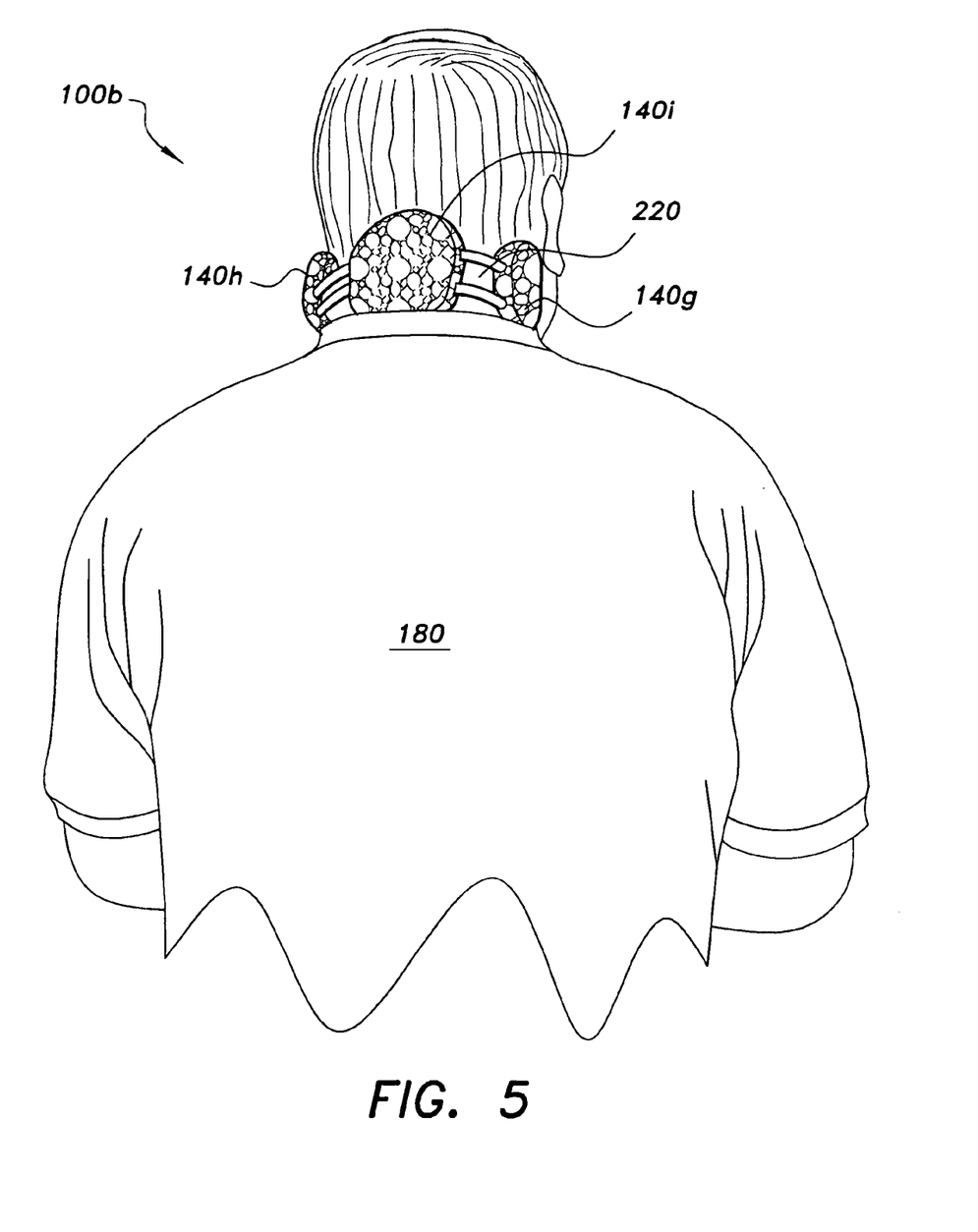
FIG. 5 is a rear view of the hot stone therapy apparatus of FIG. 4.
Figure 6:
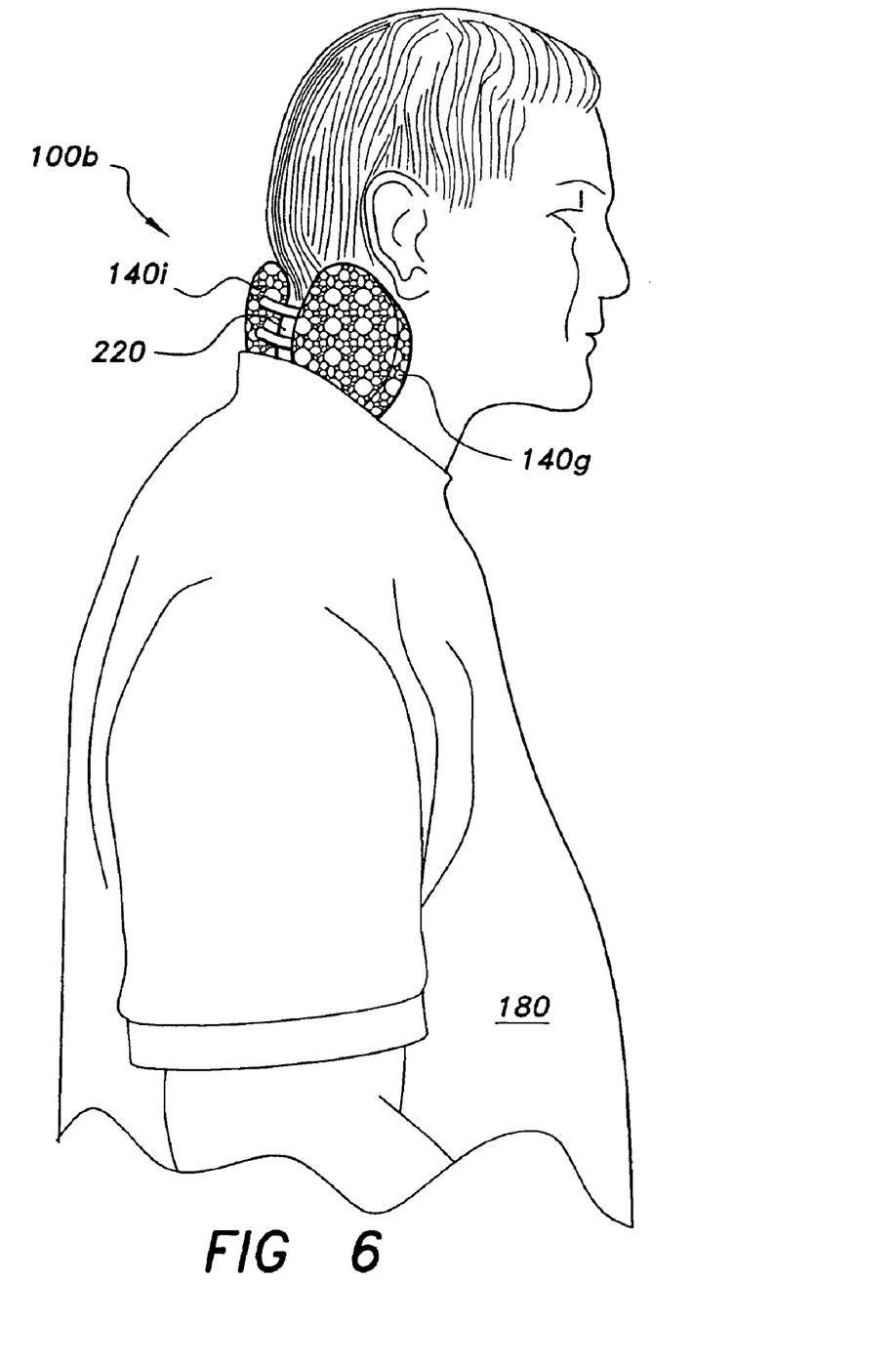
FIG. 6 is a side view of the hot stone therapy apparatus of FIG. 4.

The stones 140 are preferably heated by placing the device 100 in hot water. The stones 140 absorb heat energy from the hot water and after absorbing a sufficient amount of heat energy the device 100 may be fitted, for example, to a person's neck 220 (FIGS. 4, 5, and 6). With regard to the term "sufficient amount of heat energy" the inventor means an amount of heat energy sufficient to heat the stones to a temperature that would not cause a burn or discomfort to a wearer 180; the prospective wearer 180 can determine a preferred stone temperature from experience or by using, for example, a thermometer to measure water temperature.

FIGS. 4, 5, and 6 are environmental perspective views of a second embodiment of the invention in which the hot stone therapy apparatus 100 takes the form of a neck hot stone therapy apparatus 100b. The neck hot stone therapy apparatus 100b is configured to apply hot stone therapy to a person's neck area 220. The device 110b comprises a center stone 140i that abuts against the rear part of the neck 220. The end flanking stones 140g and 140h abut against the opposite sides of the neck 220.

Figures 7, 8:
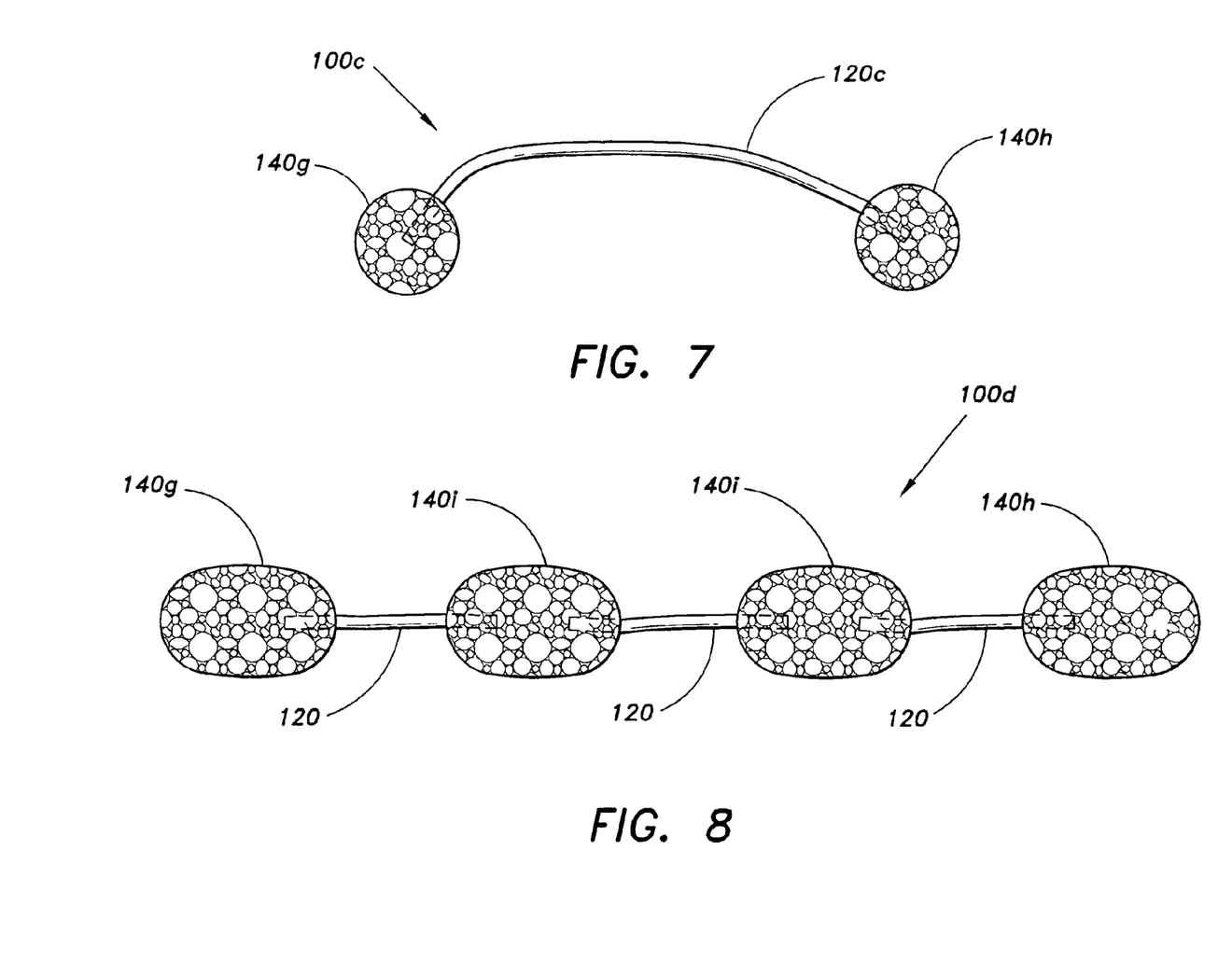
FIG. 7 shows a hot stone therapy apparatus adapted to apply hot stone therapy to a person's hip according to a third embodiment of the invention.
FIG. 8 shows a hot stone therapy apparatus adapted to apply hot stone therapy to a person's spine according to a fourth embodiment of the invention.

FIG. 7 shows a third embodiment of the present invention in which the device 100 takes the form of a hip hot stone therapy apparatus 100c. The hip embodiment 100c comprises a single elongated flexible member 120b with opposite ends embedded in end stones 140g and 140h.

FIG. 8 shows a fourth embodiment of the present invention in which the device 100 takes the form of a spine hot stone therapy apparatus 100d. The spine embodiment 100d comprises an at least one elongated flexible member 120 each with opposite ends embedded in a middle 140i or one of the end stones 140g or 140h.

Figure 9A:
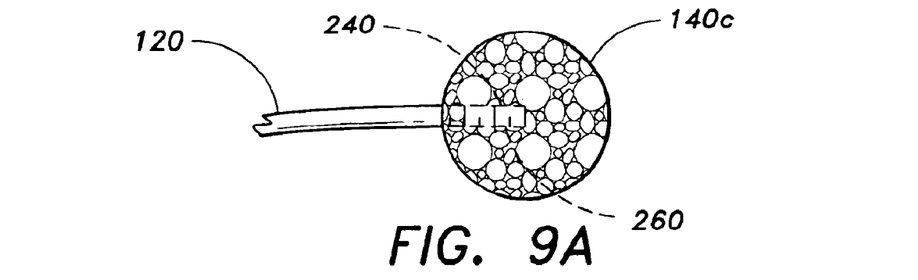
FIG. 9A shows an elongated flexible member screwed into a stone according to the invention.

FIGS. 9A, 9B, 9C, 9D and 9E show various mechanisms of attachment between the end 240 of an elongated flexible member 120 and a stone 140c. FIG. 9A shows a stone 140c with a blind hole 260 therein; the blind hole 260 has a threaded interior. The end 240 of the elongated flexible member 120 comprises a complementary thread that is screwed into the blind hole 260 thereby attaching the elongated flexible member 120 to the stone 140c. This form of attachment may be summarized as a drill and screw mechanism of attachment.

Figure 9B:
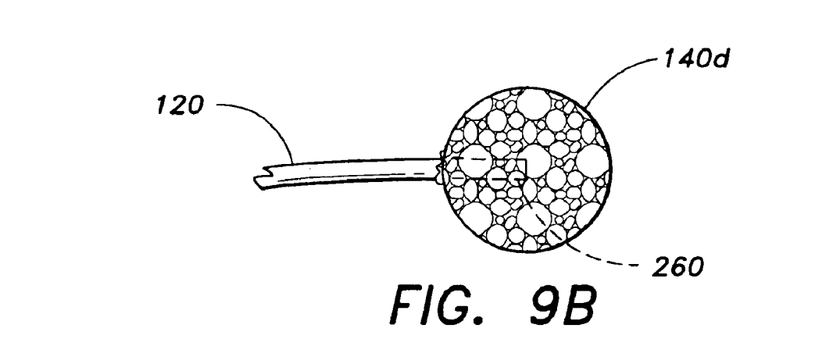
FIG. 9B shows an elongated flexible member glued into a stone according to the invention.

FIG. 9B shows a stone 140d with a blind hole 260 therein; the blind hole 260 lacks a threaded interior. The end of the elongated flexible member 120 is glued into the blind hole 260 thereby attaching the elongated flexible member 120 to the stone 140d. This form of attachment may be summarized as a drill and glue mechanism of attachment.

Figure 9C:
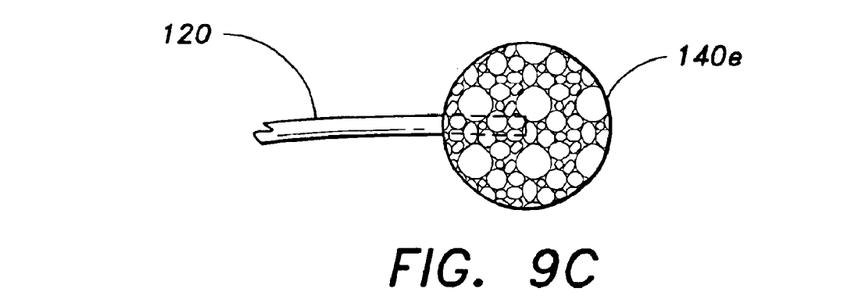
FIG. 9C shows a stone pressure fitted into a stone according to the invention.

FIG. 9C shows a stone 140e with a blind hole 260 therein; the blind hole 260 also lacks a threaded interior. The end of the elongated flexible member 120 is pressure fitted into the blind hole 260 thereby attaching the elongated flexible member 120 to the stone 140e. This form of attachment may be summarized as a drill and pressure fit mechanism of attachment.

Figure 9D:
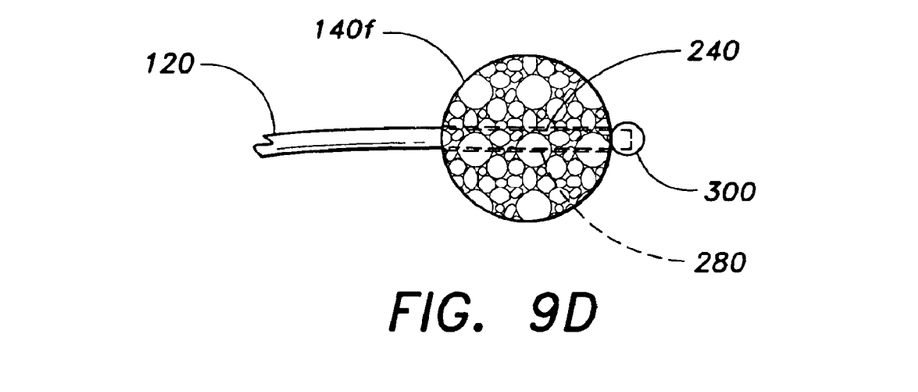
FIG. 9D shows a stone fitted through a stone according to the invention.

FIG. 9D shows a stone 140f with a hollow through bore 280. The end of the elongated flexible member 120 passes through the through bore 280 and defines an anchor 300 to keep the member 120 attached to the stone 140f. This form of attachment may be summarized as a drill and anchor mechanism of attachment. Thus, the at least one elongated flexible member 120 can be attached to the stones 140 in a variety of ways.

The invention is also directed to a process for producing a hot stone therapy apparatus adapted to provide hot stone therapy to a person. The process comprises the steps: (1) providing at least one elongated flexible member; (2) providing a plurality of molds at predetermined positions along the at least one elongated flexible member such that the at least one elongated flexible member travels through at least one of the molds; (3) filling the molds with a stone mix capable of hardening to form artificial stones, wherein the artificial stones are capable of storing heat energy; and (4) hardening the stone mix in the molds to provide hardened artificial stones at predetermined positions along the at least one elongated flexible member to provide the hot stone therapy apparatus for applying hot stone therapy to a person.

Figure 10:
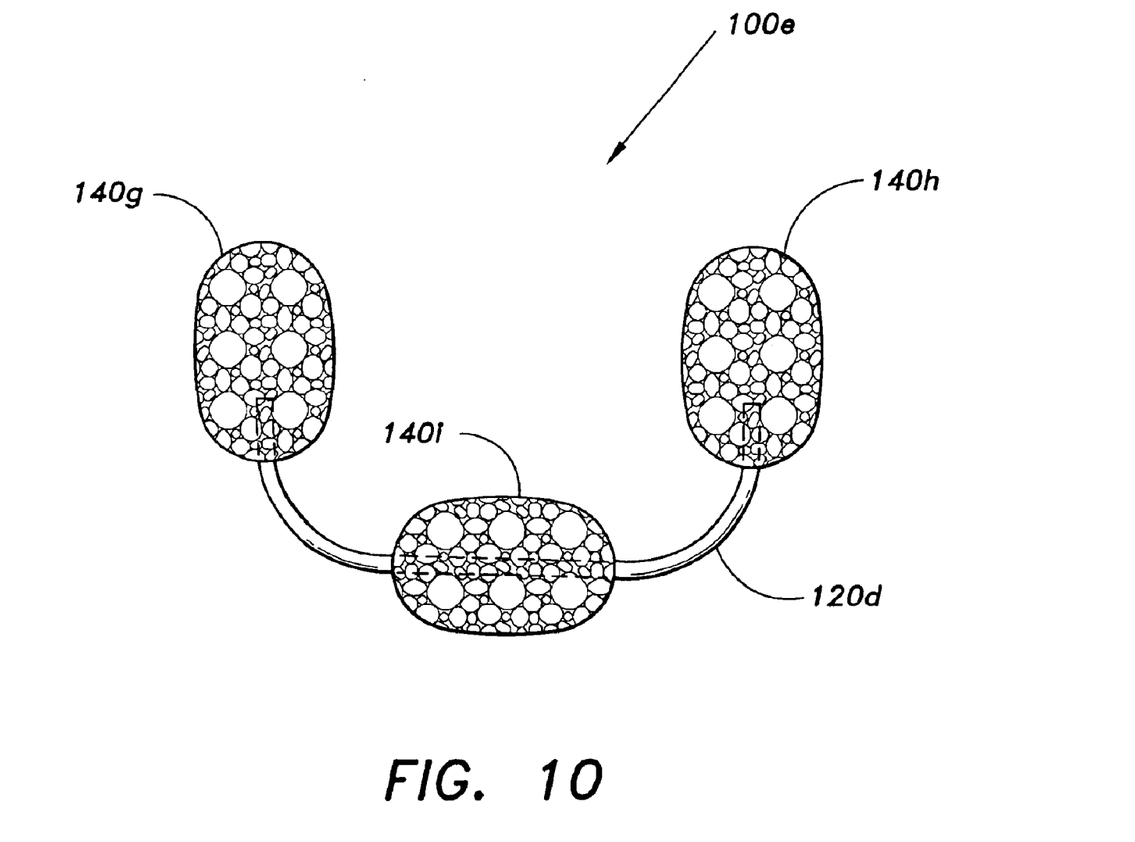
FIG. 10 shows a hot stone therapy apparatus with a plurality of stones disposed along a single continuous elongated flexible member according to the invention.

It should be understood that a mold may be provided at each opposite end of the at least one elongated flexible member such that the ends of the at least one elongated flexible member terminate inside the end molds as shown, for example, in FIG. 10.

In an alternative embodiment of the process for producing a hot stone therapy apparatus, the step of providing at least one elongated flexible member further comprises providing two substantially parallel-elongated flexible members.

FIG. 10 shows a hot stone therapy apparatus 10e produced by the above process, wherein the hot stone therapy apparatus 100e comprises a plurality of artificially molded stones disposed along a single continuous elongated flexible member 120d, the opposite ends of the elongated flexible member 120d are shown buried in molded end stones 140g and 140h. The single continuous flexible member 120d travels completely through the middle molded stone 140i. The apparatus 100e is suitable for use as a collar or neck hot stone therapy apparatus.

Figure 11:
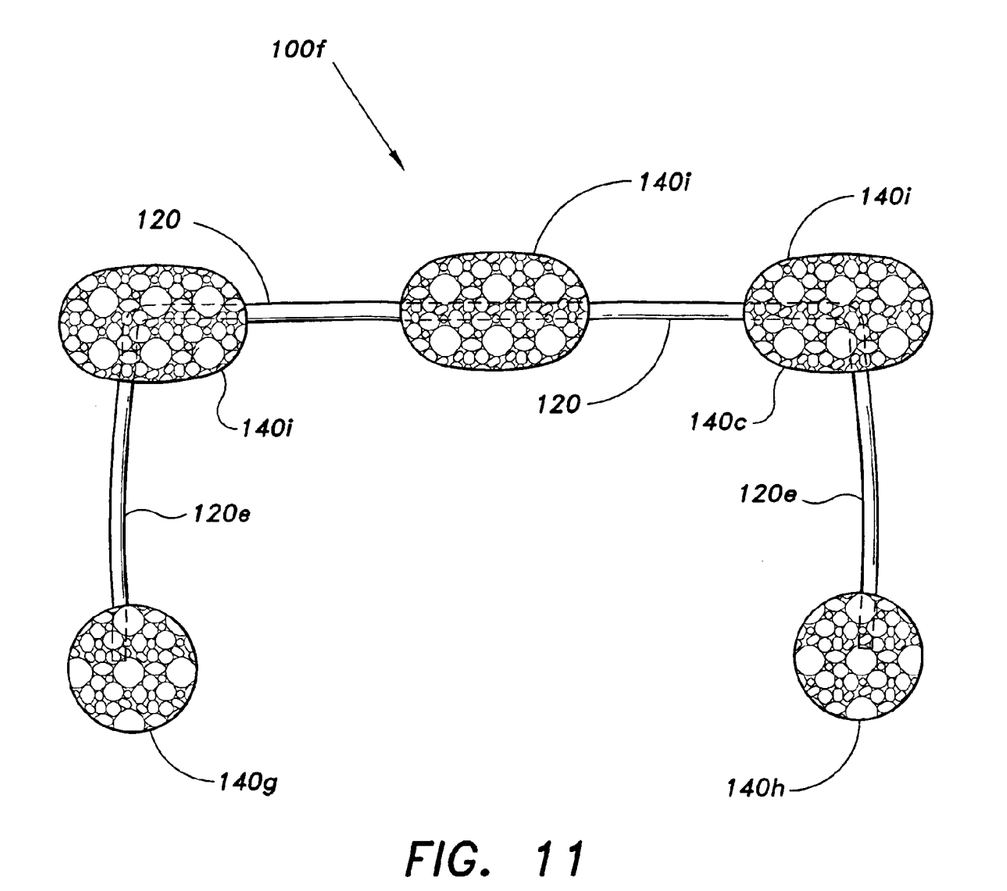
FIG. 11 shows a hot stone therapy apparatus with a plurality of artificial stones disposed along a single continuous elongated flexible member according to the invention.

FIG. 11 shows a hot stone therapy apparatus 100f produced by the above process, wherein the hot stone therapy apparatus 10f comprises a plurality of artificially molded stones disposed along a single continuous elongated flexible member 120e, the opposite ends of the elongated flexible member 120e are shown buried in artificial end stones 140g and 140h. The single continuous flexible member 120e travels completely through the middle stones 140i. The apparatus 100f is suitable for use as a shoulder hot stone therapy apparatus.

Figure 12:
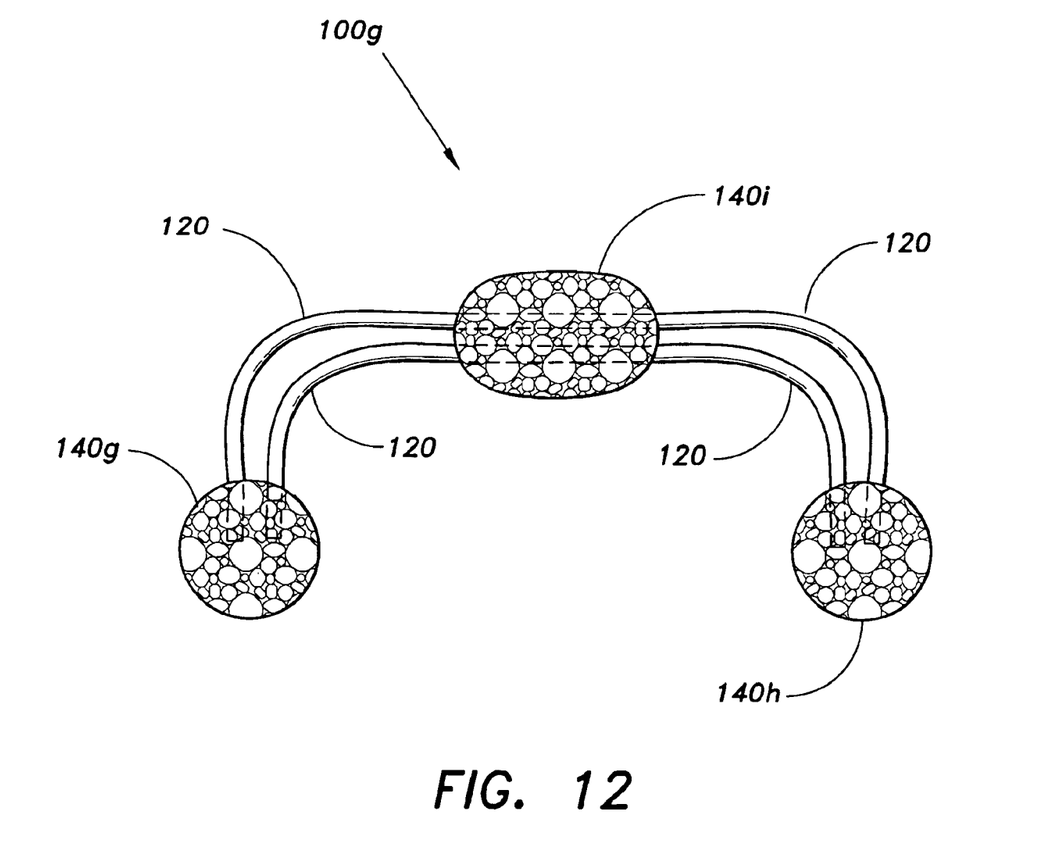
FIG. 12 shows a hot stone therapy apparatus with a plurality of artificial stones disposed along two substantially parallel and continuous elongated flexible members according to the invention.

FIG. 12 shows a hot stone therapy apparatus produced by the above process, wherein the hot stone therapy apparatus 100g comprises a plurality of artificially molded stones disposed along two substantially parallel and continuous elongated flexible members 120f and 120g. The apparatus 100g is suitable for use as a collar or neck hot stone therapy apparatus.

Figure 13:
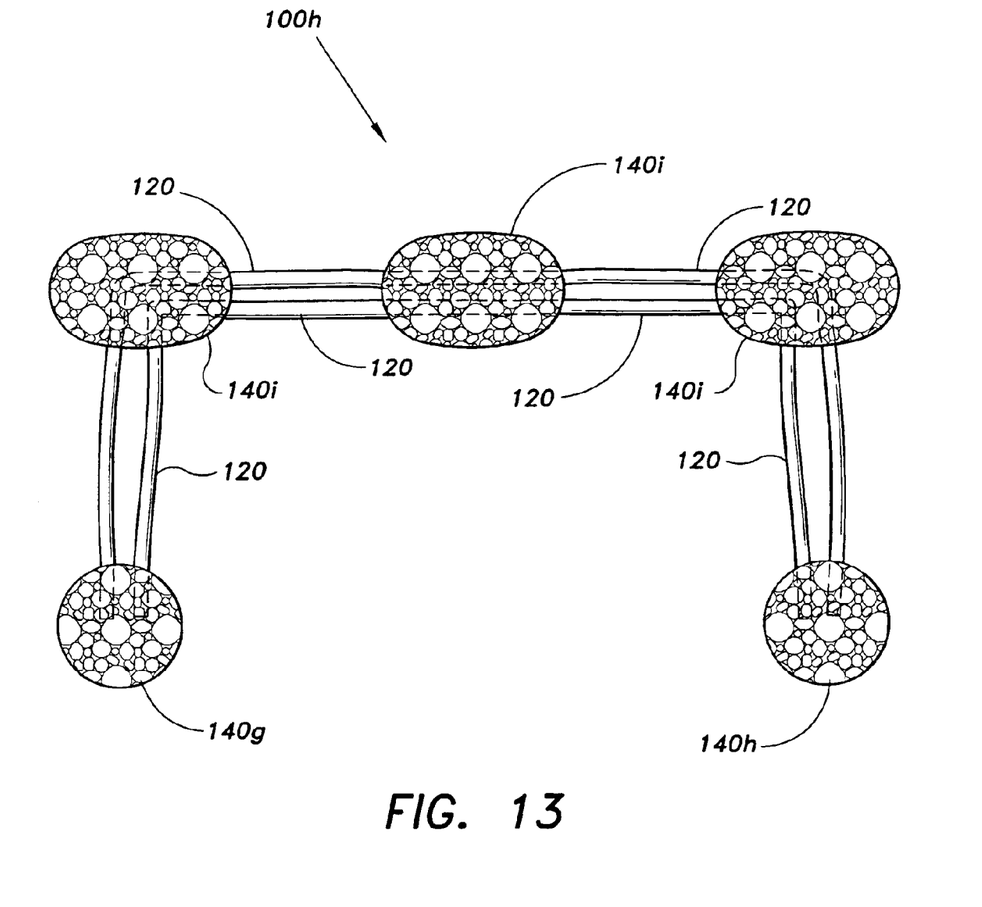
FIG. 13 shows a hot stone therapy apparatus with a plurality of artificial stones disposed along two substantially parallel and continuous elongated flexible members according to the invention.

FIG. 13 shows a hot stone therapy apparatus produced by the above process, wherein the hot stone therapy apparatus 10h comprises a plurality of stones disposed along two substantially parallel and continuous elongated flexible members 120h and 120i. The apparatus 100h is suitable for use as a shoulder hot stone therapy apparatus.

Figure 14:
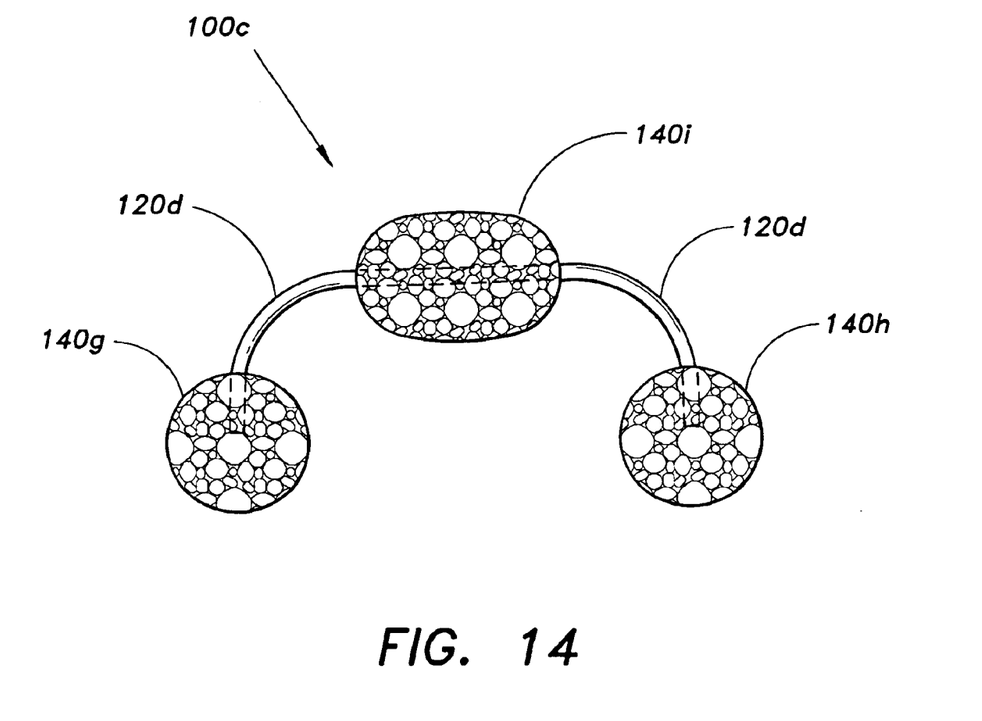
FIG. 14 shows a hot stone therapy apparatus with a plurality of artificial stones disposed along a single continuous elongated flexible member according to the invention.

FIG. 14 shows a hot stone therapy apparatus produced by the above process, wherein the hot stone therapy apparatus 100i comprises a plurality of artificially molded stones disposed along a single continuous elongated flexible member in the form of a strip 120d having a generally rectangular cross-section; thus, the flexible elongated member may take various forms. The apparatus 100i is suitable for use as a collar or neck hot stone therapy apparatus.

It is to be understood that the present invention is not limited to the embodiments described above, but encompasses any and all embodiments within the scope of the following claims.

I claim:

1. A hot stone therapy apparatus for applying hot stone therapy to a neck and shoulders of a person, comprising:

at least two segments of an elongated flexible member; and a plurality of stones connected in series to each other by the at lease two segments of the elongated flexible member to provide the hot stone therapy apparatus, said plurality of stones including two end stones, each of the end stones consisting of a unitary body having two adjacent blind holes defined therein, wherein the at least two segments of the elongated flexible member are secured within the two adjacent blind holes of each of the end stones, wherein the stones are capable of storing heat energy, whereby the distribution of the plurality of stones permit self-application of the stones about a neck and shoulders of a person;

whereby the distribution of the plurality of stones permit self-application of the stones about a neck and shoulders of the person;

wherein the at least two segments of the elongated flexible member is sufficiently stiff to keep the stones in place about the neck and shoulders of the person; and the plurality of stones consists of five stones, the two end stones adapted to rest against a chest region of the person, the other three stones adapted to rest on an upper back region of the person about the neck and shoulders;

whereby, the two end stones are not directly connected to each other and whereby, the person can walk about while wearing the shoulder hot stone therapy apparatus.

* * * * *